United States Patent
Kolp et al.

(10) Patent No.: US 7,385,694 B2
(45) Date of Patent: Jun. 10, 2008

(54) TRIBOLOGICAL DEBRIS ANALYSIS SYSTEM

(75) Inventors: Joseph P. Kolp, North Canton, OH (US); Thomas J. Sebok, Tallmadge, OH (US); Douglas E. Russell, Canal Fulton, OH (US)

(73) Assignee: Lockheed Martin Corporation, Akron, OH (US)

( * ) Notice: Subject to any disclaimer, the term of this patent is extended or adjusted under 35 U.S.C. 154(b) by 329 days.

(21) Appl. No.: 10/897,799

(22) Filed: Jul. 22, 2004

(65) Prior Publication Data

US 2005/0002030 A1    Jan. 6, 2005

Related U.S. Application Data

(63) Continuation-in-part of application No. 10/162,380, filed on Jun. 4, 2002, now Pat. No. 7,019,834.

(51) Int. Cl.
*G01N 15/02*    (2006.01)
(52) U.S. Cl. ...................................... 356/335
(58) Field of Classification Search ................ 356/335, 356/601; 382/224
See application file for complete search history.

(56) References Cited

U.S. PATENT DOCUMENTS

| | | | |
|---|---|---|---|
| 3,198,064 A | 8/1965 | Moore | 88/14 |
| 3,713,743 A * | 1/1973 | Simms | 356/338 |
| 3,879,129 A * | 4/1975 | Inoue | 356/335 |
| 3,947,121 A | 3/1976 | Cotter et al. | 356/38 |
| 4,302,754 A * | 11/1981 | Magee et al. | 340/631 |
| 4,393,466 A | 7/1983 | Deindoerfer et al. | 364/415 |
| 4,492,461 A * | 1/1985 | Jones et al. | 356/38 |
| 4,582,684 A | 4/1986 | Vogel et al. | 422/57 |
| 4,661,913 A * | 4/1987 | Wu et al. | 702/19 |
| 4,804,267 A | 2/1989 | Greenfield | 356/335 |
| 4,807,267 A | 2/1989 | Rifu et al. | 378/7 |

(Continued)

FOREIGN PATENT DOCUMENTS

EP    0 556 971 A3    2/1993

(Continued)

OTHER PUBLICATIONS

"CCD vs. CMOS: Facts and Fiction", Litwiller, D.; Photonics Spectra, Jan. 2001; Laurin Publishing & Co. Inc. p. 3, col. 2, Reliability section.

*Primary Examiner*—Roy M Punnoose
(74) *Attorney, Agent, or Firm*—Renner Kenner Greive Bobak Taylor & Weber

(57) ABSTRACT

A tribological debris analysis system alternately including a general purpose computer used in conjunction with an imaging device and an illumination delivery system, or a circuit board integrating an embedded processor with the imaging device used in conjunction with the illumination delivery system. The illumination delivery system includes a bypass conduit connected to the machine under evaluation, an optical flow cell, a pump for pumping a fluid through the optical flow cell connected to the bypass conduit, and a laser for illuminating the fluid flowing through the optical flow cell. The imaging device detects debris and sends information representative of the debris to the general purpose computer or the embedded processor. The general purpose computer or the embedded processor classifies the debris according to size, generates shape features of the imaged debris and identifies a type of object wear based upon the shape features.

23 Claims, 11 Drawing Sheets

U.S. PATENT DOCUMENTS

| | | | |
|---|---|---|---|
| 4,847,206 A * | 7/1989 | Heinz | 436/63 |
| 5,030,421 A | 7/1991 | Muller | 422/102 |
| 5,098,661 A | 3/1992 | Frohelich et al. | 422/102 |
| 5,241,189 A | 8/1993 | Vandagriff et al. | 250/575 |
| 5,506,501 A * | 4/1996 | Fogel et al. | 324/204 |
| 5,519,793 A * | 5/1996 | Grannes | 382/266 |
| 5,572,320 A * | 11/1996 | Reintjes et al. | 356/335 |
| 5,594,544 A | 1/1997 | Horiuchi et al. | 356/73 |
| 5,719,666 A * | 2/1998 | Fukuda et al. | 356/72 |
| 5,760,911 A * | 6/1998 | Santschi et al. | 356/442 |
| 5,766,957 A | 6/1998 | Robinson et al. | 436/165 |
| 5,780,865 A | 7/1998 | Miura et al. | 250/573 |
| 5,790,246 A * | 8/1998 | Kuhnell et al. | 356/72 |
| 5,883,721 A | 3/1999 | Gilby et al. | 356/440 |
| 6,104,483 A | 8/2000 | Sebok et al. | 356/244 |
| 6,115,490 A * | 9/2000 | Platsch | 382/141 |
| 6,184,983 B1 * | 2/2001 | Yamaguchi et al. | 356/335 |
| 6,598,464 B1 * | 7/2003 | Rossi | 73/53.05 |
| 6,691,557 B1 * | 2/2004 | Rice | 73/53.07 |
| 6,928,861 B1 * | 8/2005 | Rice | 73/61.42 |
| 7,019,834 B2 * | 3/2006 | Sebok et al. | 356/335 |
| 7,106,374 B1 * | 9/2006 | Bandera et al. | 348/308 |
| 2001/0036322 A1 * | 11/2001 | Bloomfield et al. | 382/276 |
| 2002/0142504 A1 * | 10/2002 | Feldman et al. | 438/30 |
| 2003/0030810 A1 | 2/2003 | Sebok et al. | 356/436 |
| 2003/0223061 A1 | 12/2003 | Sebok et al. | 356/335 |
| 2004/0218798 A1 * | 11/2004 | Abdel-Fattah et al. | 382/133 |

FOREIGN PATENT DOCUMENTS

| | | |
|---|---|---|
| EP | 0644 414 A3 | 8/1994 |
| EP | 1245 945 A2 | 3/2002 |
| GB | 2 116 704 A | 1/1979 |
| GB | 2378 526 A | 2/2003 |
| JP | 62-112034 | 5/1987 |
| JP | 7-218417 | 8/1995 |
| WO | WO 95/12118 | 5/1995 |

* cited by examiner

TRIBOLOGICAL DEBRIS ANALYSIS SYSTEM

CROSS REFERENCE TO RELATED APPLICATION

This application is a continuation in part of U.S. patent application Ser. No. 10/162,380, filed Jun. 4, 2002 now U.S. Pat. No. 7,019,834.

TECHNICAL FIELD

The present invention relates generally to fluid inspection systems. More particularly, the invention relates to a system to ensure accurate imaging of debris viewed through an optical flow cell. Specifically, the invention relates to a system that controls various components in the system and the exchange of data between those components.

BACKGROUND ART

It is known to provide fluid sampling devices using optical near-field imaging as disclosed in U.S. Pat. No. 5,572,320, which is incorporated herein by reference. Such a device is employed to determine the quantity, size, characteristics, and types of particulate matter in fluids. Examples of fluids which are monitored in such a system are lubricating oils used in engines and rotating machinery; hydraulic fluid used in various machinery; and fluids used in industrial quality control, food processing, medical analysis, and environment control. In its most common use, such a device monitors engine oil for metal particulates or flakes, wherein a size, number, and shape of particulates correspond to an engine condition and can alert one to particular problems with the engine. Non-metallic debris in the fluid can also be detected, such as fibers, sand, dirt and rust particles. Predicting failure is critically important in aircraft engines to avoid accidents and loss of life.

The early stages of engine wear cause small particulate matter, of about 50 microns or less in size, to be generated. These particulates have characteristic shapes indicative of the type of wear produced by specific wear mechanisms. As the wear process progresses, the amount and size of particulates increase. Accordingly, imaging and identifying smaller particles allows early identification of faults, thus, allowing more time for corrective maintenance and preventing unexpected catastrophic failures.

The advantage of the aforementioned system over previous systems is readily apparent when one considers that the previous systems only measured the amount of light passing through the material-laden oil, but gave no consideration as to the particular shape of the material. As best seen in FIGS. 1A-G, the various types of images rendered by a known system can provide a clear indication of the types of problems that are likely to occur based upon the shape and structure of the debris monitored. For example, in FIG. 1A, sliding wear particles are shown and these particles are believed to be caused by metal-to-metal contact due to overloading, misalignment, high speed and/or low oil viscosity. The debris shown in FIG. 1B represents fatigue wear particles which are gear or bearing pieces generated due to surface stress factors such as excessive load, contamination, and the like. FIG. 1C shows cutting wear particles that are generated by surface gouging, two body cutting due to break-in, misalignment, and three body cutting due to particle abrasion. FIG. 1D shows oxide particles which are caused by contamination, and red oxide caused by water or insufficient lubrication of the subject machinery.

It will also be appreciated that certain elements may be in the oil that generate false readings. These elements are classified and may be disregarded by the imaging system. For example, as shown in FIG. 1E, fibers are shown which are normally occurring or may be caused by improper sample handling. In particular, fibers can be from mishandling the fluid which generate false readings. But, valid readings of fibers may be indicative of problems in the system. For example, a filter or composite bearing may be disintegrating. In any event, occurrences of fibers are monitored. Instrument problems due to incomplete removal of air bubbles are represented in FIG. 1F. Finally, FIG. 1G shows flow lines which are a result of instrument problems caused by insufficient replacement of a new sample.

Known tribological debris analysis systems consist of a fluid sample that is connected to a pumping device. The pump is actuated and the fluid is drawn through an optical flow cell which is illuminated by laser light. A discrete input/output board connected to a dedicated computer system controls operation of the pump and the laser in a coordinated manner. An analog camera positioned opposite the laser light obtains an analog video image of particles passing through the optical flow cell. The dedicated computer system processes the analog video by sending the video signal to a digitizer which converts the signal to a digital image. The computer system processes the digital image to determine the shape and size of the particles rendered by the system. About ninety percent of the computer system's processing time is dedicated to pixel level processing associated with the analysis of an image and the detection of object elements. Accordingly, the system requires that the raw video input be directly sent to the general purpose computer for processing and analyzing of the images. It has been found that the known system is quite expensive and easily overloaded. Since the computer system is a dedicated device, it is limited in its ability to analyze the particles and detect any trends associated with the particles. Moreover, the known computer system is unable to check the lifetime history of a particular device when periodic samples are taken from the device. Therefore, such prior art systems, although effective, are not easily adapted for large scale use and implementation.

Moreover, it has been found that tribological debris analysis systems have significantly increased utility if their size is decreased. Previous tribological debris analysis systems have been utilized in laboratory settings, and the fluids being analyzed have had to be carried from the field to these tribological debris analysis systems. Because these tribological debris analysis systems are not located near the source of the fluids to be analyzed, using these systems to develop realtime information from analysis of the fluids has been impossible. Therefore, there is a need for a compact tribological debris analysis system which can be used remotely. Such a tribological debris analysis system could be modular such that it could be mounted on or coupled to a machine in order to analyze fluid samples taken directly from the machine. As such, the tribological debris analysis system could be configured to provided realtime information about the condition of the machine. The tribological debris analysis system could be configured to interface with a display device to display the condition of the machine at the location of the machine, or remotely with a computer monitoring system to display such information, further analyze such information, or correlate such information with information from other tribological debris analysis systems attached to other machines.

SUMMARY OF THE INVENTION

It is thus an object of the present invention to provide a tribological debris analysis system.

The foregoing and other objects of the present invention, which shall become apparent as the detailed description proceeds, are achieved by tribological debris analysis system, comprising a general purpose computer; and a tribological sensor system for generating data, the sensor system comprising an optical flow cell; a pump for pumping a fluid through the optical flow cell; a laser for illuminating the fluid flowing through the optical flow cell; and an imaging device for detecting debris in the fluid illuminated by the laser, and generating object segments representative of the debris and sending the object segments to the general purpose computer for analysis.

Other aspects of the present invention are attained by a tribological sensor system for imaging particles in a fluid comprising a fluid illumination delivery system for placing the fluid in a field of view; and an imaging device for detecting any particles in the field of view and generating object information representative of the particles for analysis.

Still other aspects of the present invention are attained by a computerized method for classifying particles in a fluid taken from a device, wherein the particle-containing fluid is imaged into object segments, the computerized method comprising receiving the plurality of object segments; generating a plurality of object elements from the plurality of object segments; and classifying the plurality of object elements according to predetermined characteristics.

It is another aspect of the present invention to provide a computerized method for classifying particles in a fluid taken from a device, wherein the particle-containing fluid is imaged into object information, the computerized method comprising: classifying the object information according to predetermined characteristics.

Yet another aspect of the present invention is to provide a compact modular tribological debris system which can be used remotely, wherein the system integrates an imaging device and a computer as an embedded processor on a single circuit board. The self-contained circuit board in addition to an illumination delivery system can be mounted on an individual machine, and fluid from the machine can be analyzed as the machine is operating. Thereafter, an interface connected to the embedded processor can transfer information concerning the condition of the machine developed by the embedded processor to a display device or computer monitoring system for further analysis.

These and other objects of the present invention, as well as the advantages thereof over existing prior art forms, which will become apparent from the description to follow, are accomplished by the improvements hereinafter described and claimed.

BRIEF DESCRIPTION OF THE DRAWINGS

For a complete understanding of the objects, techniques and structure of the invention, reference should be made to the following detailed description and accompanying drawings, wherein.

BEST MODE FOR CARRYING OUT THE INVENTION

Figure 1A:
FIG. 1A-G are examples of different types of particles detected by an optical debris analysis system according to the present invention.
Figure 1B:
Figure 1C:
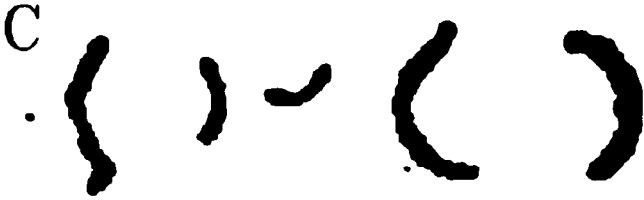
Figure 1D:
Figure 1E:
Figure 1F:
Figure 1G:
Figure 2:
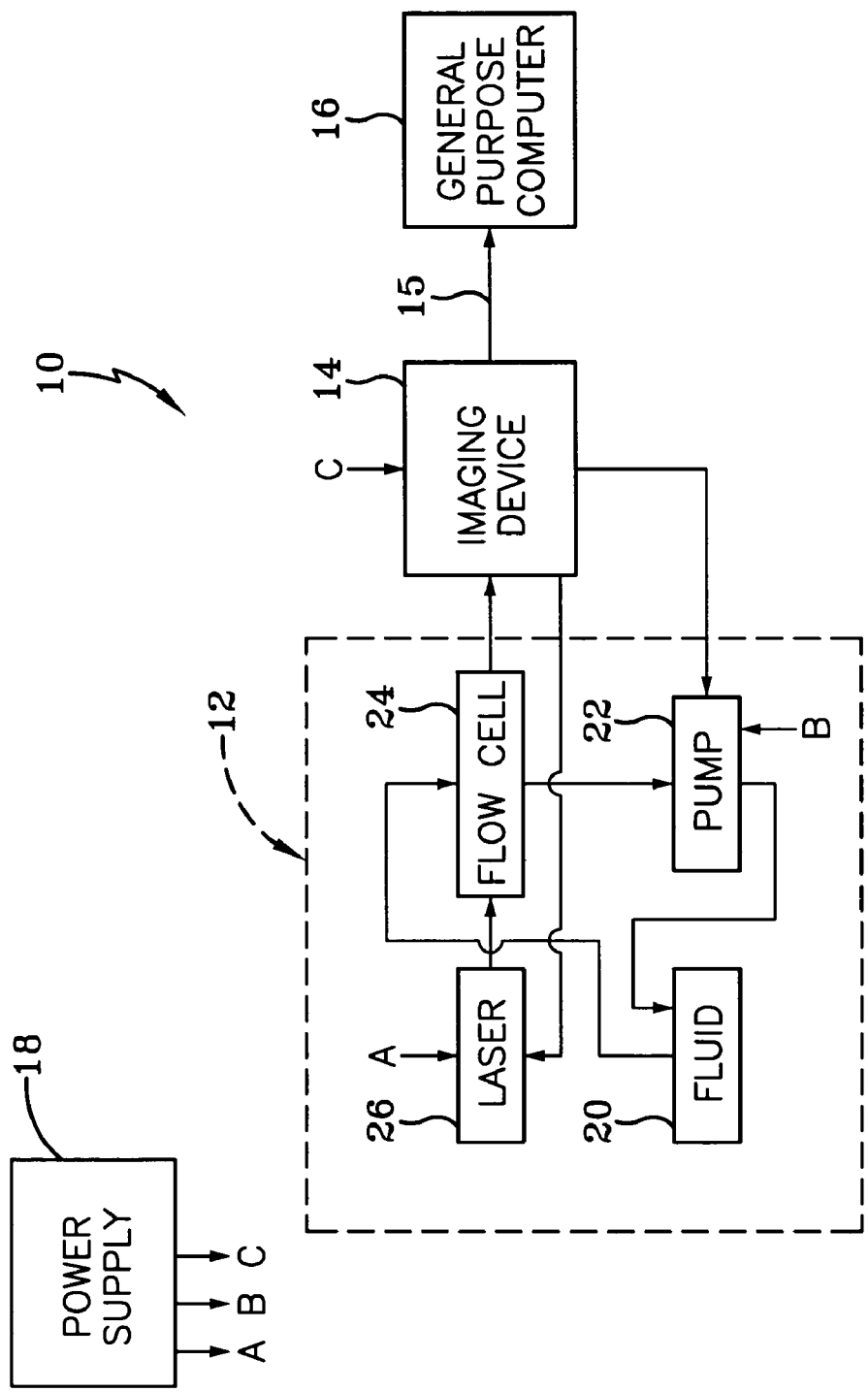
FIG. 2 is a schematic diagram of the system according to the present invention.

Referring now to the drawings and, more particularly to FIG. 2, a tribological debris analysis system according to the present invention is designated generally by the numeral 10. The system 10 includes an illumination delivery system 12 and an imaging device 14 which generates a data signal 15 received by a general purpose computer 16. A power supply 18 supplies power to the particular components of the system 10. Although a general purpose computer 16 may be used in the preferred embodiment it will be appreciated that most any computing device with the necessary memory, hardware and software could be utilized in the system 10. In all likelihood, the general purpose computer 16 is powered separately.

The illumination delivery system 12 includes a fluid container 20 for holding the fluid material to be analyzed. The fluid may be a lubricating oil used in engines and rotating machinery; hydraulic fluid used in various machinery; and fluids used in industrial quality control, food processing, medical analysis, and environmental control. Typically, the fluid sample is taken from and identified with a particular unit or device and if the device has multiple ports that particular port is identified. This information is input into the general purpose computer for cataloging purposes. In any event, the fluid container 20 is connected to a pump 22 which draws the fluid in the container through an optical flow cell 24. As the fluid is being drawn through the flow cell 24 a laser 26 illuminates one side of the flow cell 24 to generate an image that is detected by the imaging device 14. After the appropriate processing of the image, the imaging device 14 generates a data signal 15 that is received by the general purpose computer 16.

Figure 3:
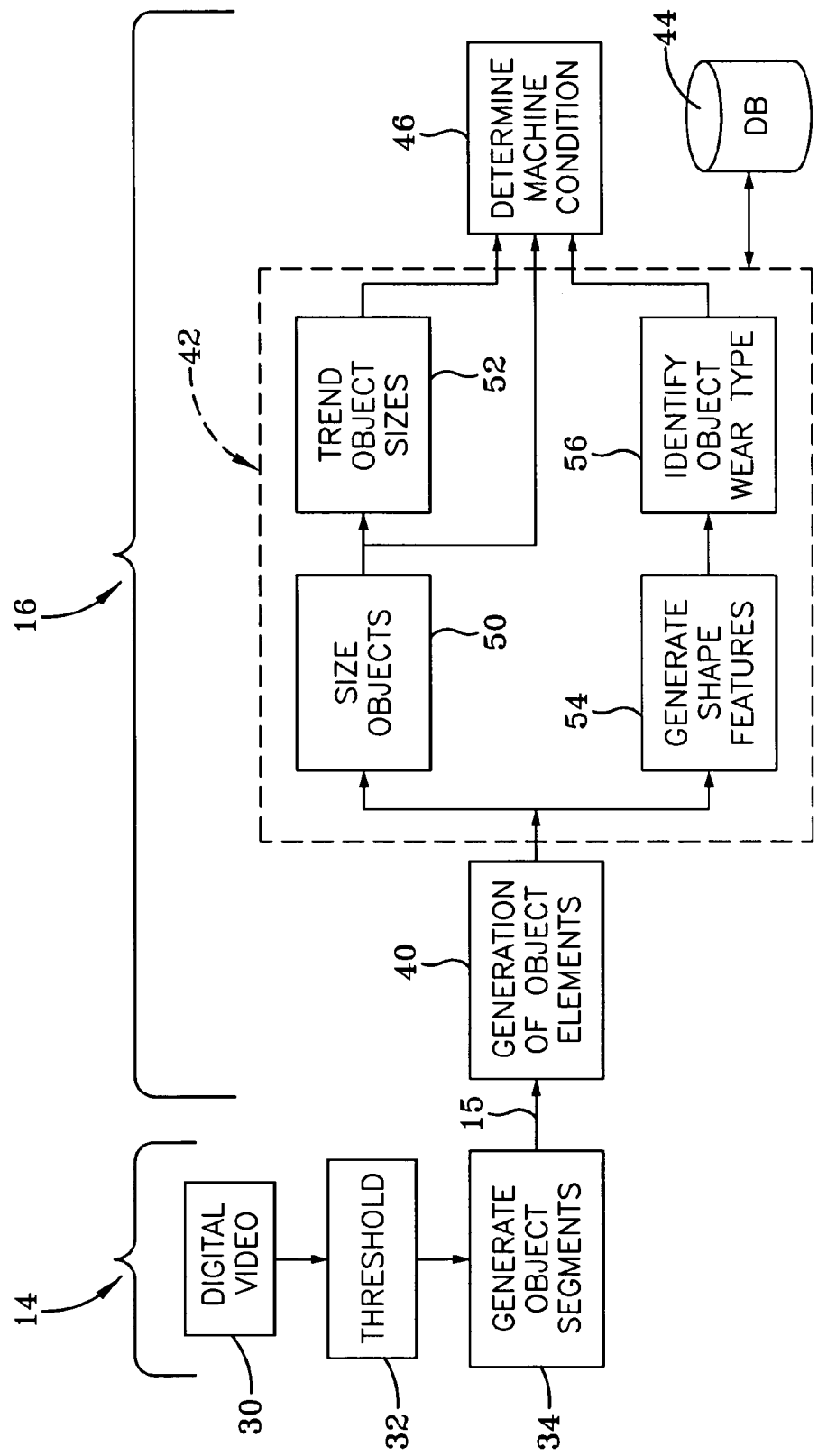
FIG. 3 is a processing flow chart showing functions of an imaging device and a general purpose computer according to the present invention.

Referring now to FIG. 3, a flow chart describing the general operational features of the system 10 is shown. The imaging device 14 generates a digital video signal at step 30. Initially, when the fluid begins flowing through the optical flow cell, an illumination map is generated. In the preferred embodiment, the illumination map comprises the first 32 frames of video to establish a base line illumination pattern.

This allows the system to take into account the characteristics of the laser beam, which is circularly polarized light, and other artifacts associated with the system. And since various types of fluid material with different opacities are likely to be tested it is important to establish a base line level of illumination for analysis of the particles contained within the fluid.

After generation of the illumination map, the system performs a thresholding step 32. The digital video signal is initially provided at 256 levels of gray corresponding to the illumination map. The threshold step converts the 256 different levels of illumination to a bi-level image. In other words, if a particular pixel is deemed to have an intensity value in the lighter half of the 256 levels then it is designated as being an 'off' pixel. But, if the pixel is in the darker half of the spectrum then the pixel is deemed to be associated with an object and it is designated as an 'on' or darkened pixel. The thresholding process determines whether each pixel should be designated as part of an object or not. It will also be appreciated that the thresholding step could be further defined as four levels—instead of two—or however many levels are appropriate depending on the base thresholding level.

After completion of thresholding step 32, the thresholded information is used to generate object segments at step 34. An object segment is a contiguous group of pixels in a row wherein all pixels in the group have the 'not off' value. In other words, the object segments are individual rows of an object detected which are defined by a row number, a column start position, and a column stop position. The object segments are included in the data 15 that is sent to the general purpose computer 16.

The general purpose computer 16 receives the object segments in the data 15 and generates a set of object elements at step 40. It will be appreciated that the object elements are configured object segments which have some continuity between adjacent rows of pixels. Formation of the object elements may also be configured by filtering routines as deemed appropriate or based upon the past history of particles detected. In any event, after the generation of the object elements they are classified at step 42 according to different types of particles or debris as discussed in the description of FIGS. 1A-G. Upon completion of the classifying step, the general purpose computer at step 44 may access a hierarchical database 44 for comparing known types of particles with those particles detected in the fluid. Finally, at step 46, based upon the comparison of the particles and other features, a machine condition is determined. The computer 16 may use neural networks or other algorithms to classify the particles. This information is displayed by the general purpose computer with recommendations and/or information for the purpose of determining the wear conditions of the machinery from which the fluid was obtained. And if fluid is drawn from several different ports of the machinery this information can also be correlated and stored.

The classifying step 42 includes the steps of sizing the objects detected at step 50 which correlates to the expected useful life of the machinery from which the fluid was drawn. The size of the objects may be input directly to step 46 to determine the machine condition. In addition, the object sizes are input to process step 52 to determine the trend of the object sizes. In other words, at step 52 if there is an increase in object size or a decrease in object size this information can be detected and monitored. The trending in object sizes may also be used to analyze previous fluid samples taken from a particular port of a machine or used to compare similar machines to one another. At step 54, the general purpose computer may utilize the object elements to generate shape features which are indicative of the type of wear being experienced by the machine from which the fluid sample was drawn. This information is utilized at step 56 to identify the object wear type by comparing the shape features to those in the database. This information can be further utilized to determine the machine condition at step 46.

Figure 4:
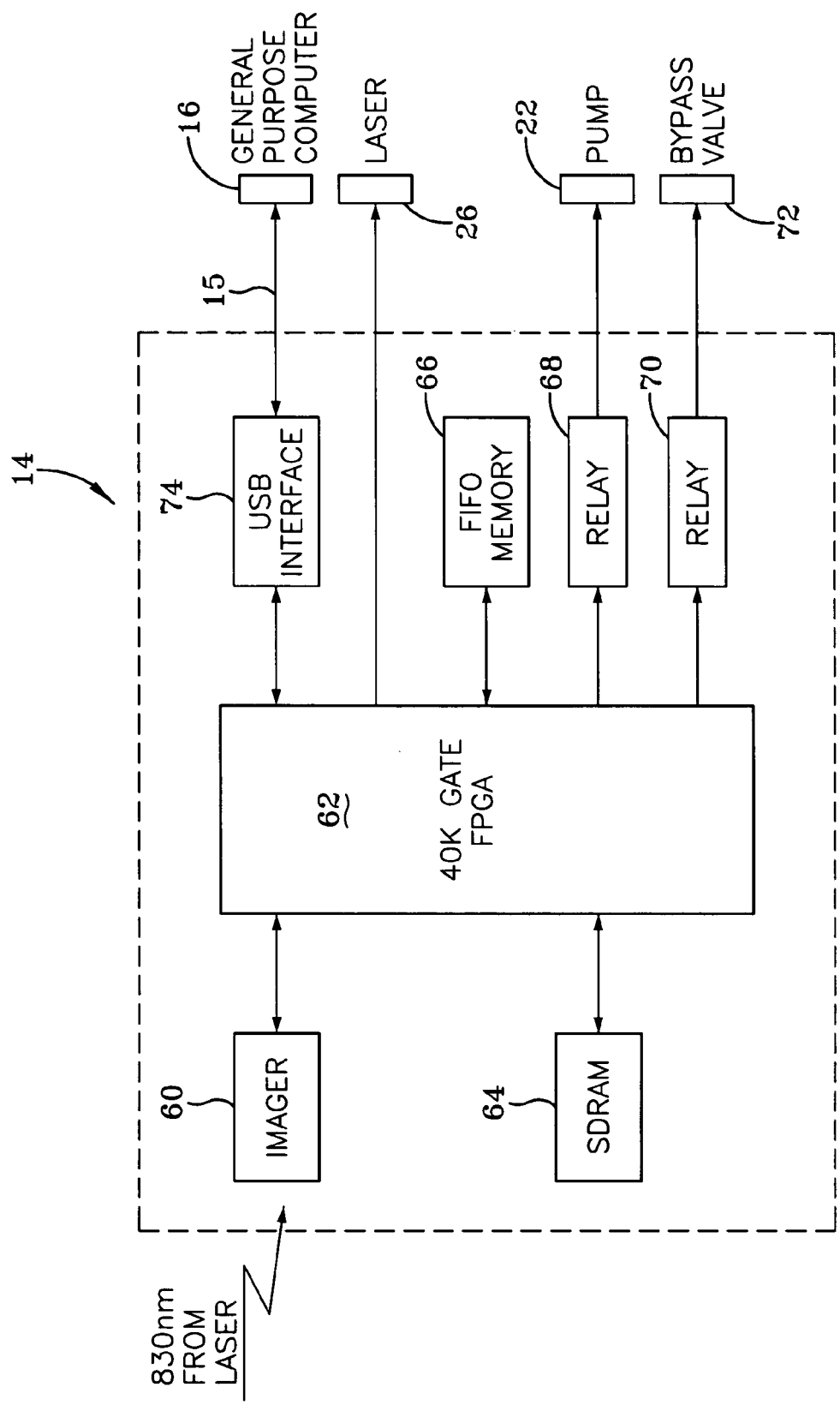
FIG. 4 is a block diagram of the imaging device according to the present invention.

Referring now to FIG. 4, the circuitry of the imaging device 14 will now be discussed. Light from the laser is projected at 830 nm through the flow cell onto a CMOS imager 60 which is 640×480 pixels and that operates at an update rate of 30 hz. The imager 60, which may also be referred to as a camera, generates a digital video signal of the laser-illuminated fluid sample. This information is transferred to a field programmable gate array 62 which performs the pixel processing, image filtering, image thresholding, segment detection and generation of global image statistics. Additionally, the array 62 functions to control the other components of the imaging device. These components include an interface device 74, which in the preferred embodiment is a universal serial bus (USB), the imager 60, the memory devices contained within the imaging device 14, the pump 22 and the laser 26. The USB interface 74 sends the object segment to the general purpose computer and receives instructions back from the general purpose computer. The array 62 also controls relays 68 that control the directional flow of the fluid through the pump 22 and a relay 70 that controls a bypass valve 72 which is utilized to "prime" the pump 22 prior to imaging any fluid flowing through the optical flow cell 24. In communication with the array 62 is a synchronous dynamic random access memory (SDRAM) device which is utilized to store the illumination map needed for thresholding the video signal. The SDRAM is a 16 by 1 megabit memory device. Of course, it will be appreciated that any appropriately sized memory device could be implemented in the present invention. Another memory device associated with the imaging device 14 is a first-in first-out (FIFO) memory device 66 used to store the data processed by the array 62 until the general purpose computer 16 is in need of it.

Figure 5:
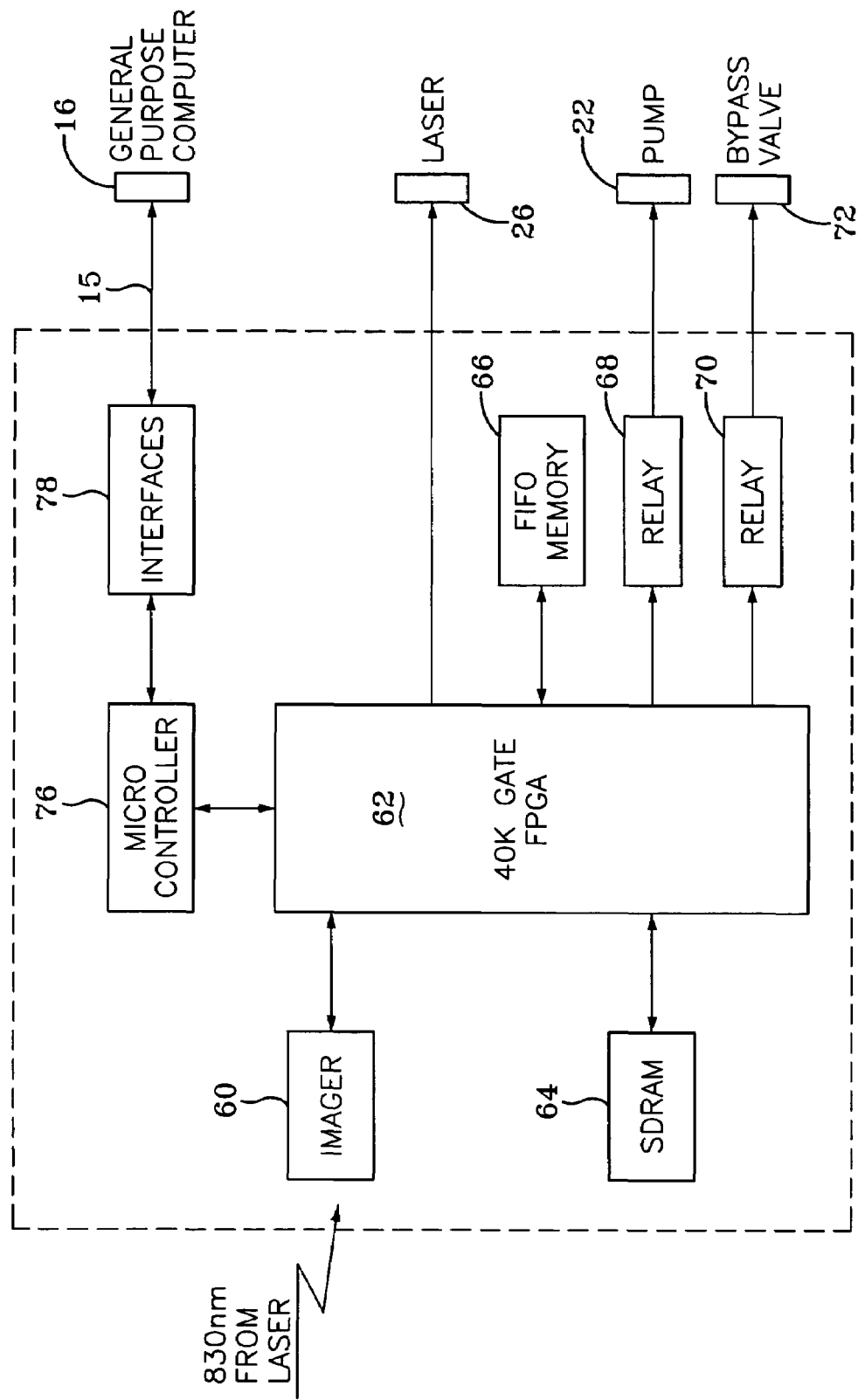
FIG. 5 is a block diagram of an alternative embodiment of the imaging device according to the present invention.

An alternative embodiment of the imaging device 14 is shown in FIG. 5. This device operates in much the same manner as the device shown in FIG. 4, but in this instance the imager 60 may be provided with a faster updating frequency. And in this embodiment a microcontroller 76 may be in communication with the array 62 to allow for different types of interface devices 78 to be in communication with the general purpose computer 16. The microcontroller 76 controls the interfaces and may take on additional object processing chores which allows for the detected segments to be converted into the object elements in the imaging device instead of by the general purpose computer. In any event, the object information transmitted to the general purpose computer will be object elements instead of object segments resulting in a further reduction in the required bandwidth and further enabling the user to use a less expensive general purpose computer or to more easily send the serial data to an appropriate computing device.

Figure 6:
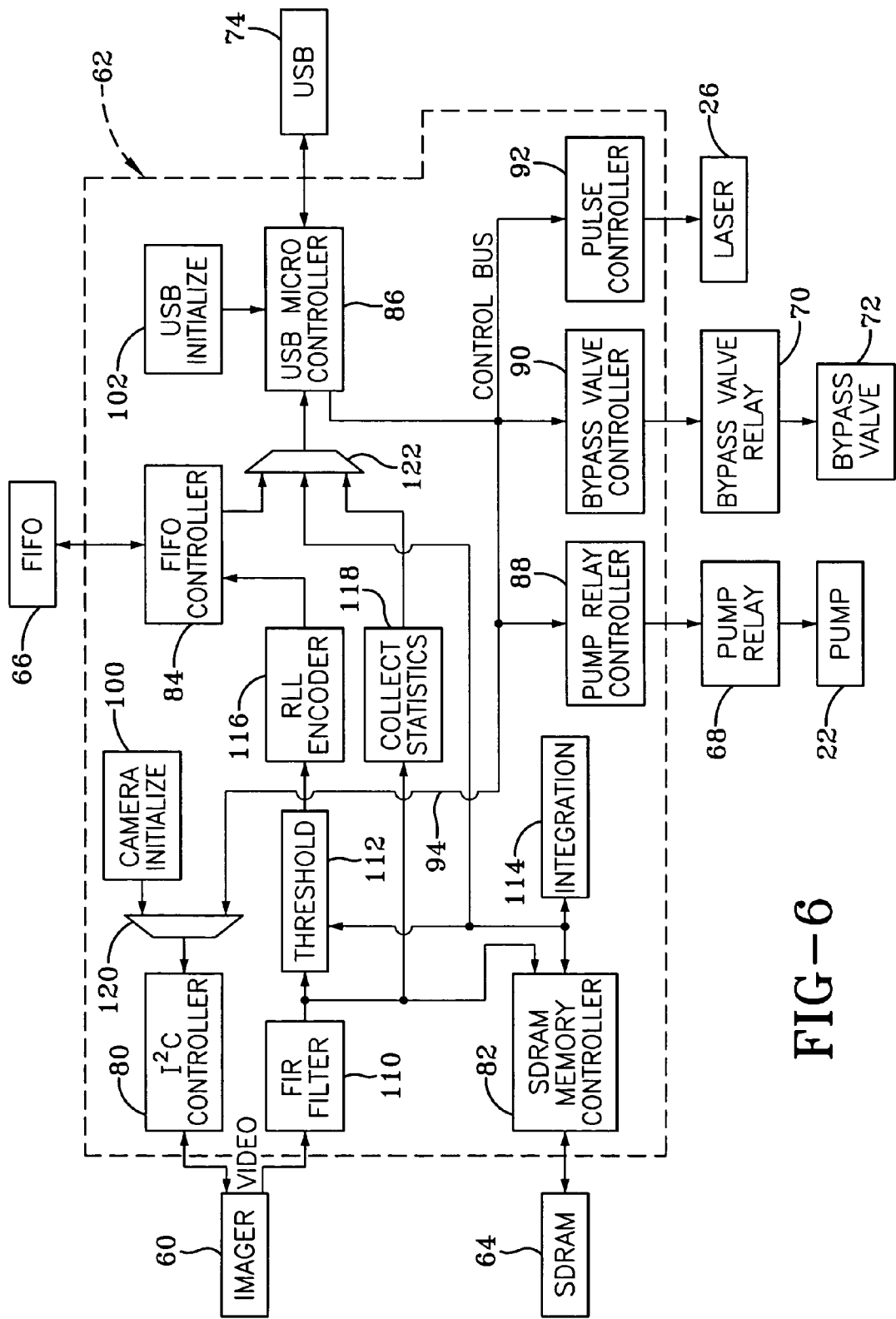
FIG. 6 is a block diagram of a field programmable gate array utilized by the system of the present invention.

Referring now to FIG. 6 a detailed schematic diagram of the array 62 is shown. As noted previously, the array 62 is in communication with the imager device 60 and memory devices 64 and 66. Output devices connected to the array include the general purpose computer 16 via the data signal 15, the pump 22, the bypass valve 72 and the laser 26. The array 62 includes a series of controllers which are utilized to control various aspects of these components that are connected to the array. In particular, the individual controllers include but are not limited to an I²C controller 80 which generates the necessary protocol to allow the programming and operation of the CMOS imager 60. Also provided is a SDRAM controller 82 which provides the necessary circuitry to provide the appropriate signals to control the operation of the SDRAM memory chip 64. Likewise, an FIFO controller 84 is responsible for controlling the operation of the first-in first-out memory 66 used to store objects segments until the computer 16 asks for them. A USB microcontroller 86 is responsible for controlling the USB interface 74 which organizes how data is sent to the general purpose computer. A pump relay controller 88, a bypass relay valve controller 90 and a pulse controller 92, which is associated with the laser 26, are also provided. The controllers 80, 86, 88, 90 and 92 are in communication with one another via a control bus 94

The array 62 may include initializing devices to facilitate the operation of the imaging device 14. In particular, a camera initializing device 100 sends appropriate signals to the I²C controller through a multiplexer 120 which also receives controller signals via the control bus 94. A second multiplexer 122 receives input signals from the FIFO controller 84 and the SDRAM memory controller 82. These signals are sent to the USB microcontroller 86 as deemed appropriate.

The array 62 may include a finite impulse response (FIR) filter used 110 to apply a high pass filter to the digital video signal. This filtered signal is then sent to a thresholding device 112 which converts the eight-bit gray level image into a bi-level image. Simultaneously, the filtered signal is sent to the SDRAM memory controller 82. The SDRAM memory controller 82 is configured to direct the SDRAM memory chip 64 to store a predetermined number of frames of the filtered signal. Ideally, the SDRAM memory chip is directed to store sixty-four (64) frames. After the SDRAM memory chip 64 has stored the predetermined number of frames, the SDRAM memory controller 82 transfers this information to an integrator 114. The integrator 114 integrates the frames together to produce an integration signal by in effect "averaging" the predetermined number of frames. For example, during the integration process, the integrator 114 adds the predetermined number of frames together, and, thereafter, divides the sum of the frames by the total number of frames added together. The integration process performed by the integrator 114 serves to effectively eliminate anomalies in the filtered signal, allows the system 10 to focus on particles in the fluid being analyzed.

The integration signal is subsequently stored in the SDRAM memory chip 64 until it is transferred by SDRAM memory controller 82 to the thresholding device 112. Upon receiving the integration signal, the thresholding device 112 compares the integration signal to the filtered signal. This comparison allows the thresholding device 112 to eliminate any anomalies in the bi-level image that is the thresholded video signal.

The filtered signal is also sent to a collect statistics circuit 118 which examines the digital video stream coming in and determines the average intensity value for each frame of video. Additionally, the collect statistics circuit 118 determines the relative amount of video saturation present. The data from the circuit 118 is sent to the USB microcontroller 86 via the multiplexer 122 and is used by the general purpose computer 16 to implement an automatic gain control routine to properly set the laser pulse width and camera gain by the controller 92 for optimal lighting of the fluid under test.

The thresholded video signal is sent by the thresholding device to a run length limited (RLL) encoder 116 which is responsible for detecting the object segments which are horizontally adjacent pixels in a row that the threshold device 112 has determined to be part of an object. Detected object elements are submitted to the FIFO memory device 66, and subsequently to the general purpose computer via the multiplexer 122.

Based upon the foregoing, the advantages of the present system are readily apparent. In particular, the present system allows for processing the digital video signal within the imaging device so as to allow for faster and more efficient processing of the images. In other words, it is now possible for the imaging device to generate 'object information'—object segments as shown in FIG. 4 or both object segments and object elements as shown in FIG. 5—that is then processed by the general purpose computer 16. The improvements discussed herein eliminate the need for a dedicated general purpose computer system to conduct all of the video image processing. Accordingly, the results can be displayed on most any off-the-shelf computing device while providing a system which is much less expensive. Additionally, the present device eliminates the need for a separate input/output board to control the general purpose computer and it removes the extra cabling and electronics needed to implement the previous system.

In another embodiment as seen in FIGS. 7-10, a tribological debris analysis system according to the present invention is designated generally by the numeral 210. System 210 is modular, and includes an illumination delivery system 212 interfaced with a circuit board 214 which includes both an imaging device 216 and an embedded processor 218. The circuit board 214 integrates the imaging device 216 for processing the image provided by the illumination delivery system 212, and the embedded processor 218 for analyzing the image processed by the imaging device 216. As such, the system 210 is more compact than previous tribological debris analysis systems, and the compact size of the system 210 allows its use in the field.

Figure 7:
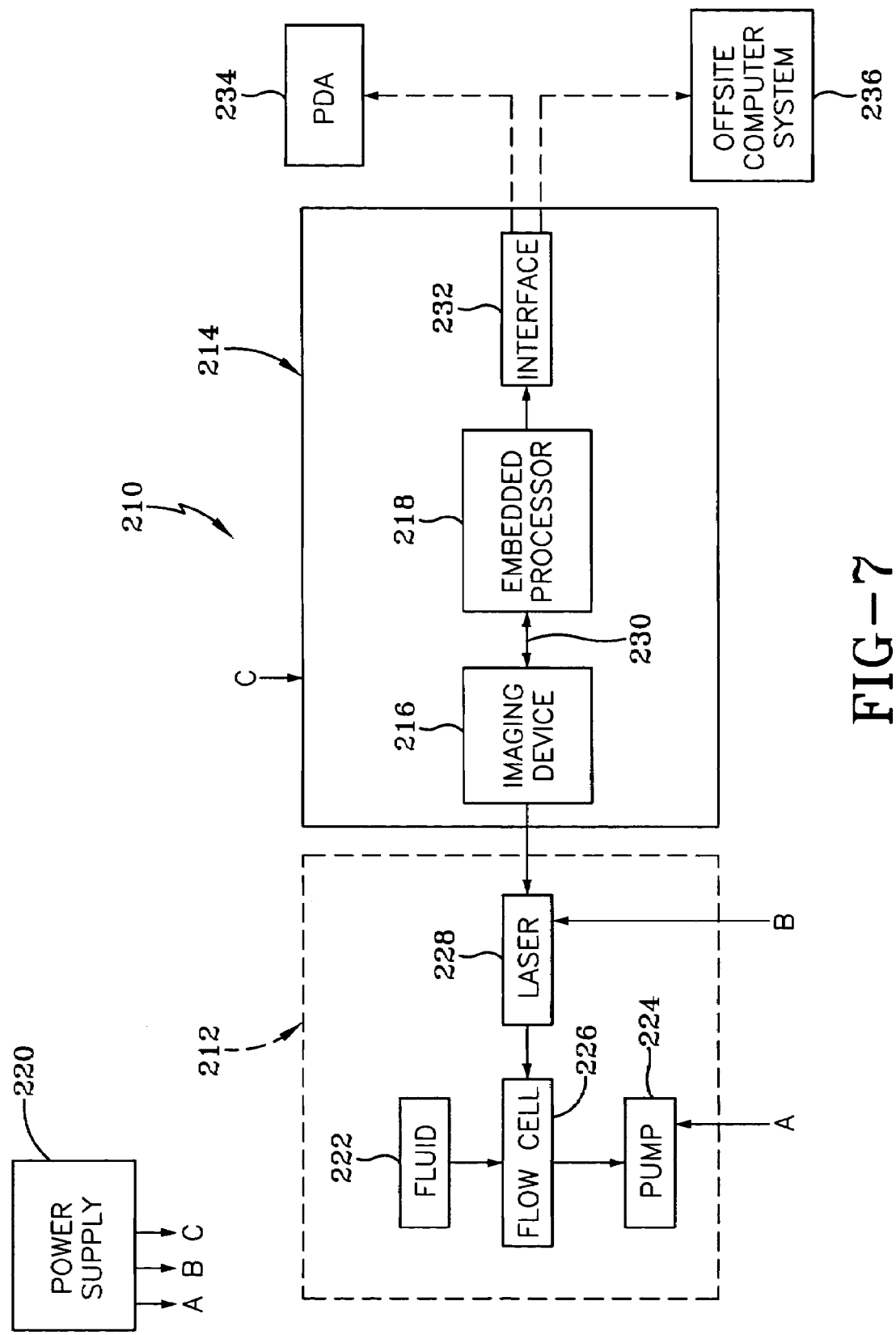
FIG. 7 is a schematic diagram of another embodiment of the system according to the present invention.
Figure 7A:
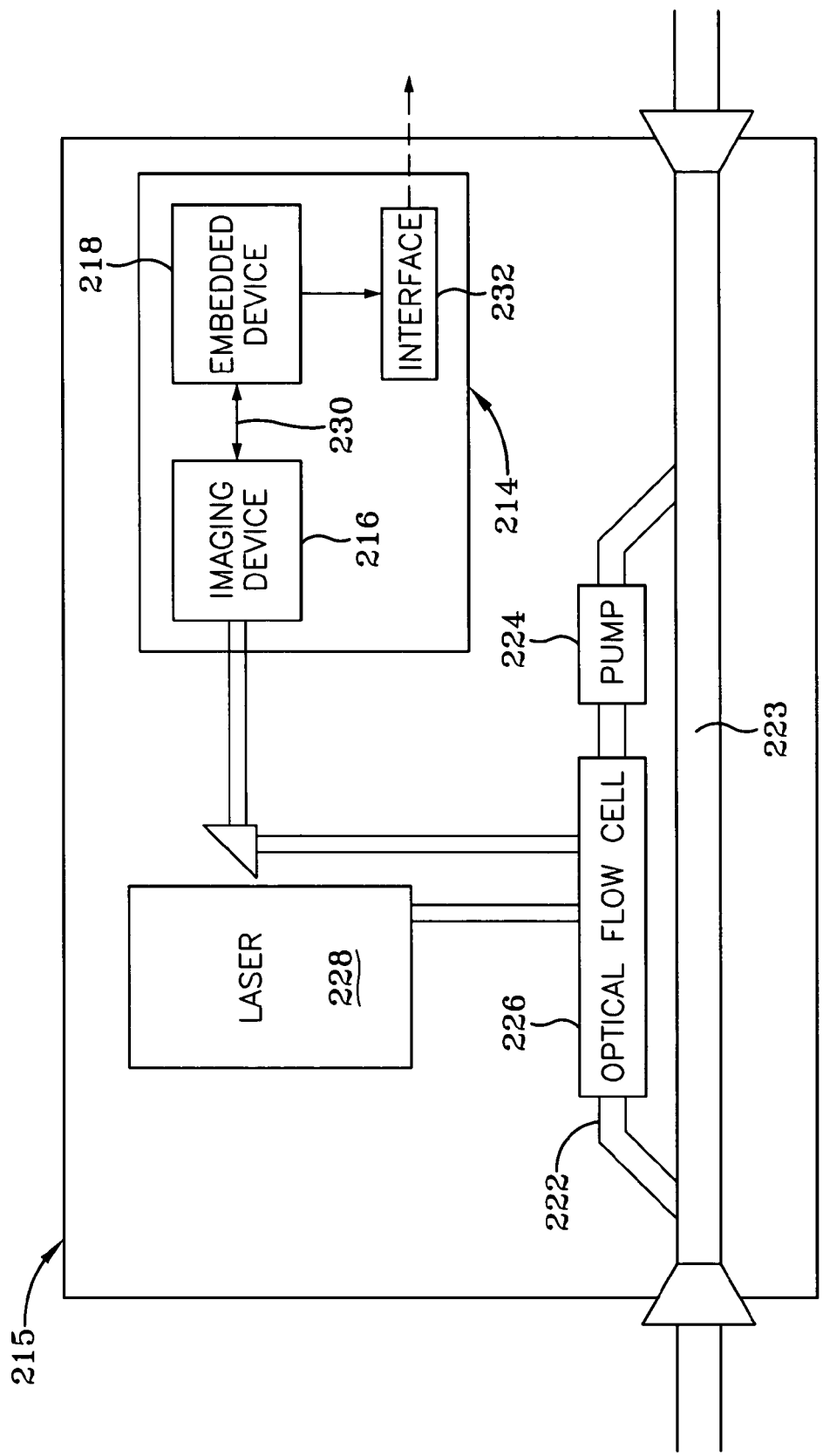
FIG. 7A is a diagram of the system depicted in FIG. 7 mounted adjacent a machine being analyzed, and interfacing with a conduit of fluid sample.

For example, the circuit board 214 is capable of being mounted on or coupled to an individual machine 215 (FIG. 7A) from which the fluid is to be analyzed is sampled. As seen in FIG. 7A, the circuit board 214 and the illumination delivery system 212 can both be mounted adjacent to the machine 215 to analyze the fluid as the machine 215 is operating. The fluids analyzed may include lubricating oils and hydraulic fluids used in various machinery; and fluids used in industrial quality control, food processing, medical analysis, and environmental control.

Using the system 210 in conjunction with the machine 215 located in the field makes it unnecessary to take fluid samples from the machine 215, and test these samples in a laboratory setting. Instead, use of the system 210 with the machine 215 saves time by developing realtime information regarding the fluid samples. As such, the use of the system 210 is significantly faster than using a tribological debris analysis system in a laboratory setting. As discussed below, a plurality of systems 210 can be used in conjunction with groups of machines in a facility to develop information about conditions of each of these machines.

A power supply 220 supplies power to the particular components of the system 210 including the illumination system 212 and the circuit board 214. To facilitate use of the system 210 at remote locations, the power supply 220 can be portable. Furthermore, to implement its use on the machine 215, the illumination delivery system 212 incorporates a bypass conduit 222 (FIG. 7A). When the system 210 is mounted on the machine 215, the bypass conduit 222 is connected to a conduit 223 (which is part of the machine 215) containing the fluid to be analyzed. The bypass conduit 222 receives the fluid so that a sample of the fluid can be processed by the illumination delivery system 212, while still allowing the machine 215 to operate in a normal manner.

Oftentimes, a pump 224 is used as part of the illumination delivery system 212 to syphon fluid from the conduit 223 into the bypass conduit 222. The pump 224 is used to draw the fluid from the conduit 223 into a optical flow cell 226 positioned in the bypass conduit 222. As seen in FIG. 7, the optical flow cell 226 is also part of the illumination system 212, and is positioned in the bypass conduit 222 such that the fluid sample can be returned to the conduit 223.

An image is generated by the illumination delivery system 212 using the optical flow cell 226. For example, a laser 228, which is part of the illumination delivery system 212, illuminates one side of the optical flow cell 226 (as the fluid sample is being drawn through the optical flow cell 226) to generate an image. Ideally, the laser 228 is a laser diode, which has a small size, and is capable of being mounted on the machine 215. After the image is detected by the imaging device 216, and, after appropriate processing of the image, the imaging device 216 generates data signal 230 which is directed to the embedded processor 218.

As discussed below, the embedded processor 218 is capable of analyzing the data signal 230 to generate information concerning the condition of the machine 215. As such, instead of using a general purpose computer to analyze the data from the imaging device 216, the embedded processor 218 is configured to determine the condition of the machine 215 from the fluid sample. Therefore, the analysis of the fluid sample can be performed at the location of the machine 215.

The circuit board 214 includes an interface 232 such as a communication port (i.e. USB, IRDA, etc.) or memory cartridge. The interface 232 offers the system 210 flexibility in communicating in different formats. For example, the interface allows the information from the embedded processor 218 to be transferred to a display device 234 or computer monitoring system 236. For example, the display device 234 could be a personal data assistant (PDA), which can be connected with the interface 232 to display the information from the embedded processor 218. As such, the information from the embedded processor 218 can be displayed at the location of the machine 215 so that it can be determined whether the machine 215 requires service.

Alternatively, the information can be transferred via the interface 232 to the computer monitoring system 236 for display, further analysis, or correlation with information from other systems 210. The ability to directly interface to the internet allows the computer monitoring system 236 to be located anywhere in the world. For example, the interface 232 can be connected directly to the computer monitoring system 236, or can be connected to an intermediate device configured to carry the information to the computer monitoring system 236.

When a plurality of systems 210 are used in conjunction with a group of machines, the computer monitoring system 236 can be configured to receive the information from these various systems 210. The realtime monitoring of groups of machines by the computer monitoring system 236 allows safety and maintenance protocols to be followed for the entire group of machines according the condition of the machines as determined by the systems 210. As such, the computer monitoring system 236 can be used to indicate when particular machines require servicing so that the downtime of the entire group of machines can be limited.

Figure 8:
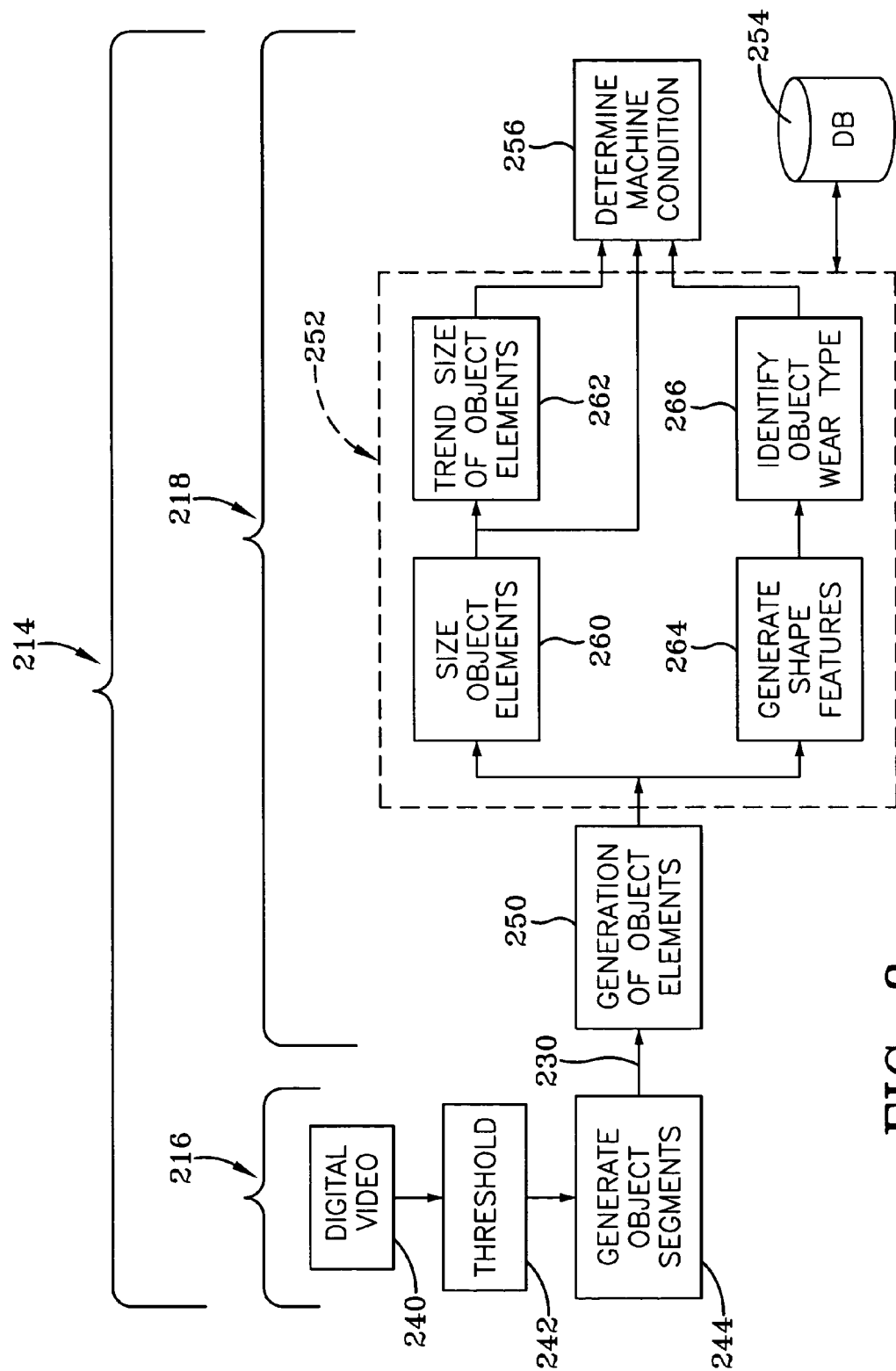
FIG. 8 is a processing flow chart showing functions of a circuit board containing a imaging device and embedded processor according to the embodiment of the system depicted in FIG. 7.

Referring now to FIG. 8, a flow chart describing the general operational features of the system 210 is shown. During processing of the image provided by the illumination delivery system 212, the imaging device 216 generates a digital video signal at step 240 in the form of the illumination map. When the fluid initially begins flowing through the optical flow cell 226, an illumination map is generated, which, in a preferred embodiment, comprises the first thirty-two frames of video. The initial illumination map establishes a base line illumination pattern that allows the system 210 to take into account the characteristics of the beam from the laser 228 (which is a circular attenuation pattern), and other artifacts associated with the system. Since various types of fluid materials with different opacities are likely to be tested, it is important to establish a base line level of illumination for analysis of the particles contained within the fluid.

After generation of the illumination map, the system imaging device 216 performs a thresholding step 242. The digital video signal is initially provided at 256 levels of gray corresponding to the illumination map. The threshold step 242 converts the 256 different levels of the illumination map to a bi-level image or multi-level image. In the case of generating bi-level image, if a particular pixel is deemed to have an intensity value in the lighter half of the 256 levels, then it is designated as being an "off" pixel. But, if the pixel is in the darker half of the 256 levels, then it is designated as being an "on" pixel. The "on" pixels are deemed to be associated with objects contained in the fluid sample. As such, the thresholding process 242 determines whether each pixel should be or should not be designated as part of an object.

After completion of the thresholding step 242, the thresholding information is used by the imaging device 216 to generate object segments at step 244. An object segment is a contiguous group of pixels in a row, wherein all pixels in the group have been designated as "on" pixels. In other words, the object segments are individual rows of an object detected during step 242 which are defined by a row number, a column start position, and a column length. The object segments are included in the data signal 230 that is sent to the embedded processor 218.

The embedded processor 218 receives the object segments in the data signal 230, and uses the object segments to generate a set of object elements at step 250. It will be appreciated that the object elements are configured object segments which have some continuity between adjacent rows of pixels. Formation of the object elements may also be configured by filtering routines as deemed appropriate or based on the past history of the particles detected. In any event, after the generation of the object elements they are classified by the embedded processor 218 at step 252 according to different types of particles or debris as discussed in FIGS. 1A-G.

Upon completion of the classifying step 252, the embedded processor 218 at step 254 may access a hierarchial database 254 for comparing known types of particles with those particles detected in the fluid. Finally, at step 256, based on the comparison of the particles and other features, a machine condition is determined. To facilitate such analysis, the embedded processor 218 may be configured to use neural networks or other algorithisms to classify the particles or debris detected. Thereafter, the embedded processor 218 is capable of generating recommendations and/or information for the purpose of determining wear conditions of the machine 215 to which the system 210 is connected. This information can be transferred via the interface 232 to display device 234 for display, and to the computer monitoring system 236 for further analysis.

The classifying step 252 includes sizing the object elements at step 260 which correlates to the expected useful life of the machinery from which the fluid was drawn. The size of the object elements may be input directly in step 256 to determine the condition of machine 215. In addition, the sizes of the object elements are inputted in step 262 to determine the trend of the object element sizes. In other words, at step 262, if there is an increase or decrease in the sizes of the object elements, this information can be detected and monitored. The trending in the sizes of the object elements is also input in step 256 to determine the condition of the machine 215, and can also be used to analyze previous fluid samples taken from a different portion of the conduit 223, or used to compare similar machines to one another. At step 264, the embedded processor 218 may use the object elements to generate shape features which are indicative of the type of wear being experienced by the machine 215. This information is used at step 266 to identify the object wear type by comparing the shape features of the object elements to those in the database 254, and this information can be further utilized to determine the condition of the machine 215 at step 256.

Figure 9:
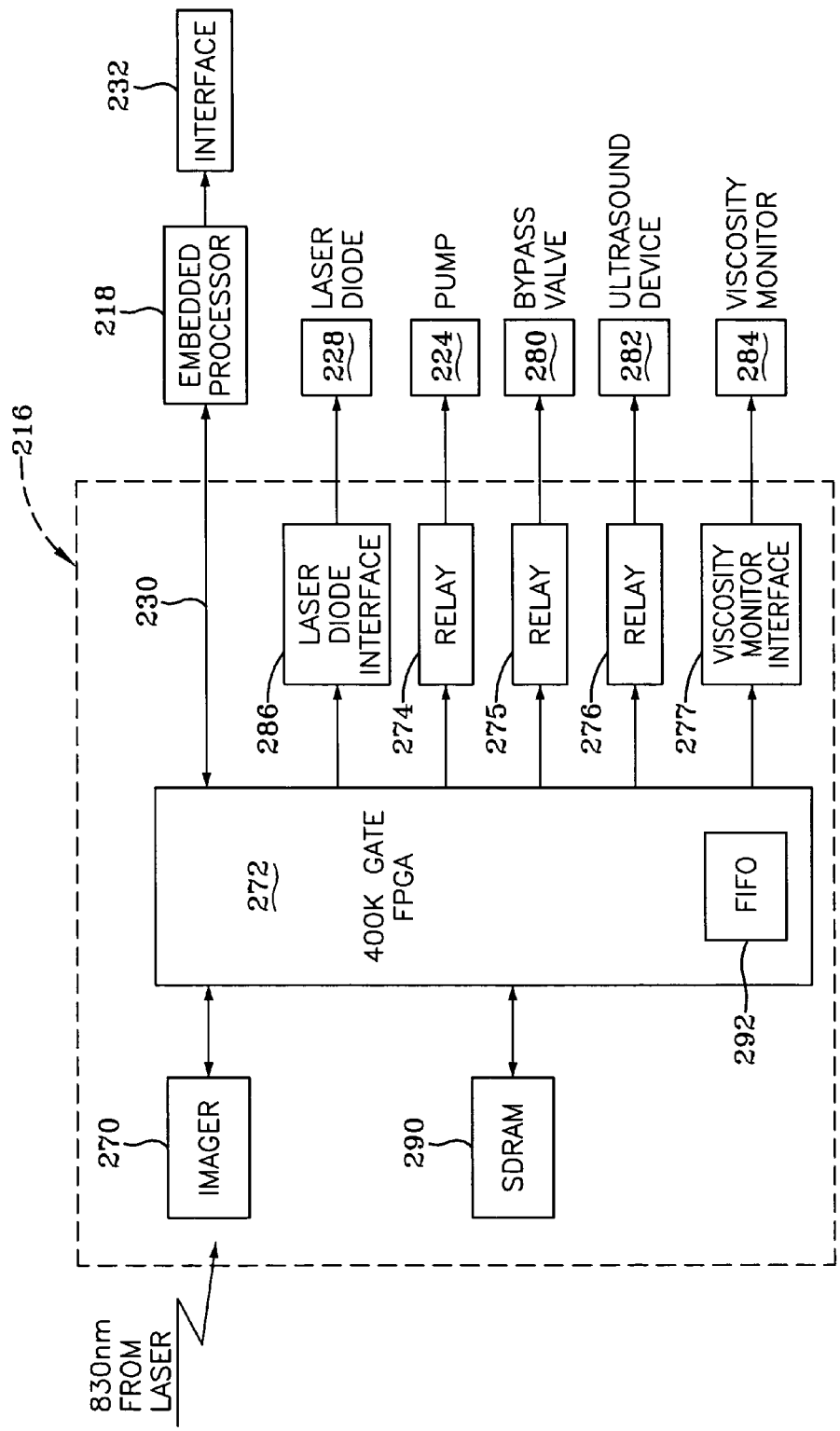
FIG. 9 is a block diagram of the imaging device according to the embodiment of the system depicted in FIG. 7.

Referring now to FIG. 9, the circuitry of the circuit board 214 will now be discussed. As discussed above, the circuit board 214 includes the imaging device 216 and the embedded processor 218 and these components function together to analyze particles within the fluid samples. For example, light from the laser 228 is projected at 830 nm through the optical flow cell 226 onto a CMOS imager 270 which is 640×480 pixels. The CMOS imager 270 is part of the imaging device 216 integrated on the circuit board 214, and operates at an update rate of about 200 Hz. The CMOS imager 270, which may also be referred to as camera, generates a digital video signal of the laser illuminated fluid sample.

The digital video signal is transferred to a field programmable gate array (FPGA) 272 which performs the pixel processing, image filtering, image thresholding, segment detection, and generation of global image statistics. Additionally, the FPGA 272 functions to control the other components of the imaging device 216 such as memory devices contained within the imaging device 216, as well, for example, the pump 224 and the laser 228. The FPGA 272 is connected to the embedded processor 218 via the data signal 230, and is also capable of receiving instructions back from the embedded processor 218.

The FPGA 272 also controls a relay 274 that controls the pump 224, and a relay 275 which controls a bi-pass valve 280 which is utilized to "prime" the pump 224. Furthermore, the FPGA 272 controls a relay 276 which controls an ultrasound device 282 (positioned along the bypass conduit 222) used to remove air bubbles from the fluid sample before entering the optical flow cell 226, and a relay 277 which controls the operation of a viscosity monitor 284 used to measure the viscosity of the fluid sample being analyzed.

Additionally, the FPGA 272 includes an interface 286 connected to the laser 228 to synchronize operation of the laser 228 and CMOS imager 270. As discussed above, the laser 228 is ideally a laser diode, however, the interface 286 is also configured to be backwardly compatible, and therefore, is capable of operating with lasers used in previous generation tribological debris analysis systems.

In communication with the FPGA 272, is a first synchronous dynamic random access memory (SDRAM) device 290 which is utilized to store the illumination map needed for thresholding the digital video signal. The first SDRAM device 290 is a 32 megabyte memory device, although, of course, it will be appreciated that any appropriately sized memory device can be implemented for such use in the present invention. Another memory device associated with the imaging device 216 is a first-in first-out (FIFO) memory device 292 used to store the data processed by the FPGA 272 until the embedded processor 218 is in need of such data. The FIFO memory device 292 can be integrated with the FPGA 272 as seen in FIG. 9.

As discussed above, the embedded processor 218 is embedded on the circuit board 214, and the data signal 230 generated by the imaging device 214 is directed thereto. Also integrated on the circuit board 214 are a second SDRAM device 300 which is utilized to store programing instructions for operation of the embedded processor 218 and a flash memory device 302 used to store the data processed by the embedded processor 218 until such data is transferred via the interface 232 to the display device 234 or computer monitoring system 236

Figure 10:
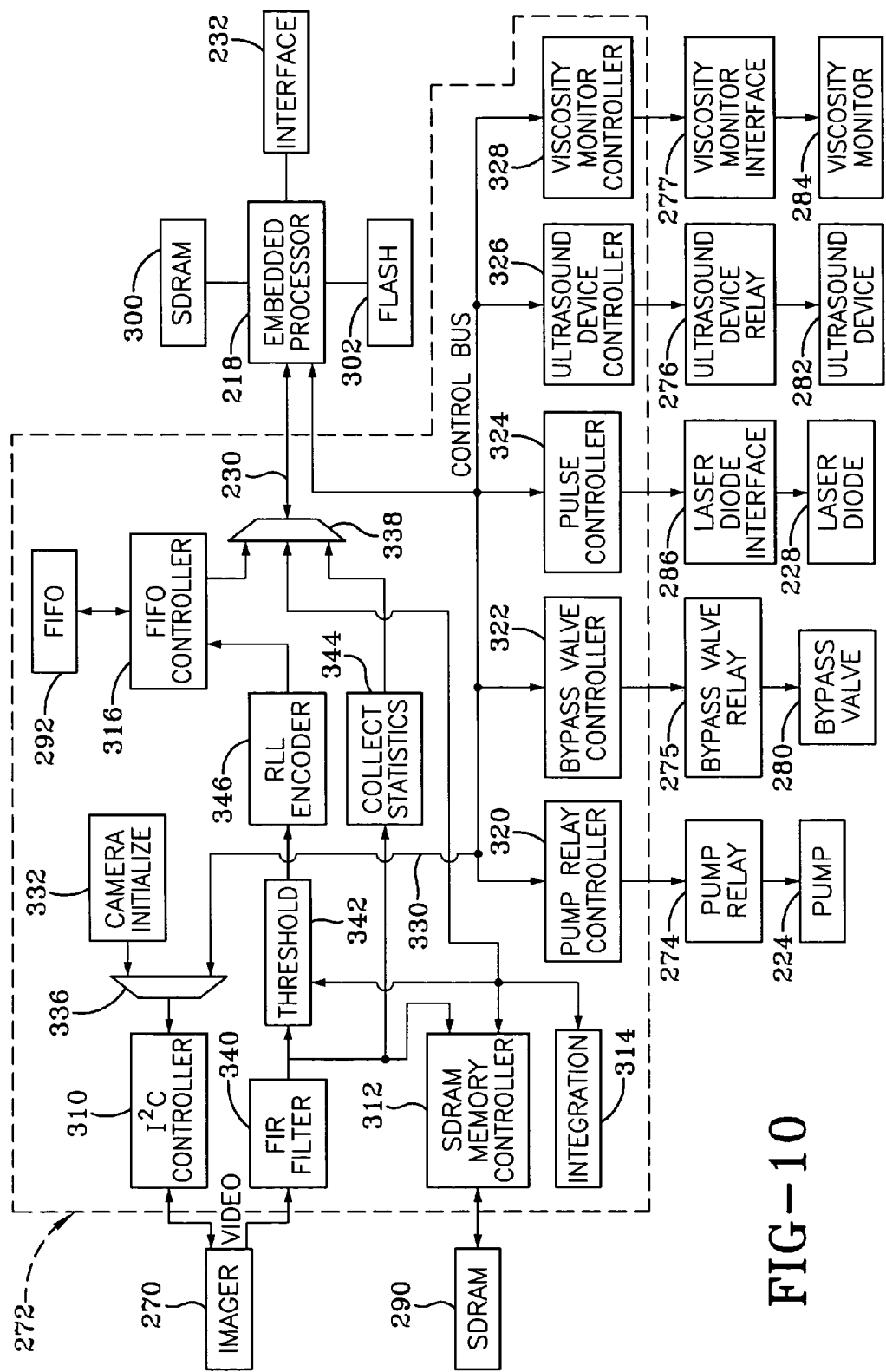
FIG. 10 is a block diagram of a field programmable gate array utilized in the embodiment of the system depicted in FIG. 7.

Referring now to FIG. 10, a detailed schematic of the FPGA 272 is shown. As noted previously, the FPGA 272 is in communication with the CMOS imager 270 and the first SDRAM memory device 290. The FIFO memory device 292 is integrated with the FPGA 272, and output devices connected to the FPGA 272 include the embedded processor 218 via the data signal 230, the pump 224, the bypass valve 280, the laser 228, the ultrasound device 282 and the viscosity device 284. The FPGA 272 includes a series of controllers which are utilized to control various aspects of these components which are connected to the array.

In particular, the individual controllers include, but are not limited to, $I^2C$ controller 310 which generates the necessary protocol to allow the programming and operation of the CMOS imager 270. Also provided is a SDRAM controller 312 which provides the necessary circuitry to generate the appropriate signals to control the operation of the first SDRAM memory device 290. Likewise, an FIFO controller 316 is responsible for controlling the operation of the FIFO memory device 292 used to store object segments until the embedded processor 218 requires them. A pump relay controller 320, a bypass valve relay controller 322, a pulse controller 324 which is associated with the laser 228, a ultrasound device relay controller 326 and a viscosity monitor interface 328 are also provided. The controllers 320, 322, 324, 326 and 328 are in communication with one another a control bus 330.

As also seen in FIG. 10, the FPGA 272 may include initializing devices to facilitate the operation of the imaging device 216. In particular, a camera initializing device 332 sends appropriate signals to the $I^2C$ controller 310 through a first multiplexer 336 which also receives controller signals via the control bus 330. A second multiplexer 338 receives input signals from the SDRAM controller 312 and the FIFO controller 316. These signals are sent to the embedded processor 218 as deemed appropriate.

The FPGA 272 may also include a finite impulse response (FIR) filter 340 used to apply a high pass filter to the digital video signal from the CMOS imager 270. This filtered digital video signal can then sent to a thresholding device 342 which converts the 8-bit gray level image into a bi-level image. At the same time, the filtered signal is sent to the SDRAM memory controller 312. The SDRAM memory controller 312 is configured to direct the SDRAM memory chip 290 to store a predetermined number of frames of the filtered signal. Ideally, the SDRAM memory chip is directed to store sixty-four (64) frames. After the SDRAM memory chip 290 has stored the predetermined number of frames, the SDRAM memory controller 312 transfers this information to an integrator 314. The integrator 314 integrates the frames together to produce an integration signal by in effect "averaging" the predetermined number of frames. For example, during the integration process, the integrator 314 adds the predetermined number of frames together, and, thereafter, divides the sum of the frames by the total number of frames added together. The integration process performed by the integrator 314 serves to effectively eliminate anomalies in the filtered signal, and allows the system 210 to focus on particles in the fluid being analyzed.

The integration signal is subsequently stored in the SDRAM memory chip 290 until it is transferred by SDRAM memory controller 312 to the thresholding device 342. Upon receiving the integration signal, the thresholding device 342 compares the integration signal to the filtered signal. This comparison allows the thresholding device 342 to eliminate any anomalies in the bi-level image or multi-level that is the thresholded video signal.

The filtered digital video signal is also sent to a collect statistics circuit 344. The collect statistics circuit 344 examines the filtered digital video signal stream to determine the average intensity value for each frame of video. Additionally, the collect statistic circuit 344 determines the relative amount of video saturation present. The data from the collect statistics circuit 344 is sent to the embedded processor 218 via the second multiplexer 338, and is used by the embedded processor to implement an automatic gain control routine to properly set the laser pulse width and camera gain by the pulse controller 324 for optimal lighting of the sample fluid being tested.

Furthermore, the thresholded video signal from the thresholding device 342 is sent to a run length limited (RLL) encoder 346 which is responsible for detecting the object segments (horizontally adjacent pixels in a row) that the thresholding device 342 has determined to be part of an object element. Any object elements detected by the RLL encoder 346 are submitted to the FIFO memory device 292, which, thereafter, sends such data to the embedded processor 218 via the second multiplexer 238.

Based upon the foregoing, the advantages of the system 110 are readily apparent. The integration of the imaging device 216 and embedded processor 218 on the circuit board 214 allows the system 210 to be mounted on an individual machine and perform its analysis function autonomously. As such, the illumination delivery system 212 can provide an image of a fluid sample taken directly from a bypass conduit 222 connected to such a machine, and the image can be processed by the imaging device 216, and analyzed by the embedded processor 218, while the machine is operating. Thereafter, the interface 232 allows the generated by the embedded processor 218 during analysis of the fluid sample to be transferred to a display device 234 or computer monitoring system 236.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. A tribological debris analysis system for analyzing fluids used in a machine, comprising:
   an illumination delivery system to control a pulse width of an illumination pulse generated thereby to illuminate a fluid sample maintained by the machine;
   an imaging device and an embedded processor integrated with a circuit board and coupled to the illumination delivery system to form a self-contained unit adapted to be mounted adjacent the machine, the circuit board configured to enable the embedded processor and the imaging device to communicate with one another, the imaging device positioned so that the fluid sample flows between the illumination delivery system and the imaging device, wherein the imaging device is configured to generate one or more data signals based on the images of debris in the flowing fluid sample illuminated by the illumination pulse, such that a predetermined number of debris images forms an illumination map comprising a base line illumination pattern, and wherein the embedded processor is enabled to determine and store a wear condition of the machine corresponding to the debris images based on an analysis of the data signals and the base line illumination pattern; and
   an interface coupled to the embedded processor, wherein the interface is adapted to be selectively coupled to a display device so as to transfer the stored wear condition data and the debris images from the embedded processor to the display device for display.

2. A tribological debris analysis system according to claim 1, further comprising:
   a bypass conduit adapted for connection to the illumination delivery system and adapted for connection to a machine conduit which carries a fluid to be tested by the illumination delivery system.

3. A tribological debris analysis system according to claim 2, wherein the illumination delivery system includes an optical flow cell, a pump for pumping the fluid through the optical flow cell, and a laser for supplying the illumination pulse to illuminate the fluid flowing through the optical flow cell, the imaging device detecting debris in fluid illuminated by the laser.

4. A tribological debris analysis system according to claim 3, wherein the data signal includes object segments representative of the debris.

5. The tribological debris analysis system according to claim 4, wherein the imaging device applies a threshold thereto to generate the object segments.

6. The tribological debris analysis system according to claim 3, wherein the imaging device comprises:
   a camera for generating an image from the field of view;
   a field programmable gate array for manipulating the image;
   at least one memory device connected to the field programmable gate array for storing the manipulated image; and
   an interface device connected to the field programmable gate array for exporting the manipulated image.

7. The tribological debris analysis system according to claim 6, wherein the field programmable gate array controls operation of the pump, the laser, and the camera.

8. The tribological debris analysis system according to claim 7 which can be mounted on the machine, wherein the at least one memory device is a random access memory device in communication with the field programmable gate array to store an illumination map of a plurality of the images.

9. The tribological debris analysis system according to claim 8, wherein the at least one memory device is a first-in first-out memory device in communication with the field programmable gate array to store the object information for analysis.

10. The tribological debris analysis system according to claim 2, wherein the embedded processor comprises:
   a generating component for receiving object segments from the imaging device and configuring the object segments into object elements;
   a classifying component for receiving and classifying the object elements according to predetermined characteristics; and
   an analyzing component for determining machine conditions based upon the classified object elements.

11. The tribological debris analysis system according to claim 10, wherein the classifying component classifies the object elements according to shape, wear type, element size and trends of element size.

12. The tribological debris analysis system according to claim 11, further comprising:
   a database component operative to maintain a database identifying wear properties of debris for comparison to the object elements by the classifying component.

13. A tribological debris analysis system according to claim 1, wherein the interface is configured to selectively communicate the wear condition data to a computer monitoring system for further analysis.

14. A tribological debris analysis system according to claim 13, wherein the computer monitoring system is capable of correlating information from various tribological debris analysis systems.

15. The tribological debris analysis system according to claim 1, wherein a multi-level threshold is applied to the one or more data signals identified based on said illumination map, so as to generate one or more object segments associated with debris detected by the imaging device, and wherein the multi-level threshold comprises at least two levels.

16. The tribological debris analysis system according to claim 1, further comprising an ultrasound device positioned adjacent said imaging device to remove air bubbles from the fluid sample.

17. A computerized method for classifying particles in a fluid taken from a machine, the computerized method comprising:
   providing an illumination delivery system to control a pulse width of an illumination pulse generated by a laser used to illuminate the particle containing fluid from the machine;
   providing a circuit board integrating an imaging device and an embedded processor in communication with each other to form a self-contained unit adapted to be mounted adjacent the machine, the imaging device arranged to detect the particles in the flow of fluid illuminated by the illumination pulse;
   generating a video signal from the detected image;
   applying a multi-level threshold to the video signal based upon an illumination map comprising a base line illumination pattern based on a predetermined number of frames of the detected image;
   generating a plurality of object segments from the applying step;
   generating a plurality of object elements from the plurality of object segments; and
   classifying the plurality of object elements according to predetermined characteristics.

18. The method according to claim 17, further comprising:
   determining the condition of the device based upon the classified plurality of object elements.

19. The method according to claim 17, wherein the step of classifying comprises:
   sizing the plurality of object elements.

20. The method according to claim 17, wherein the step of classifying comprises:
   sizing the plurality of object elements; and
   trending the sizes of the plurality of object elements for comparison to the sizes of object elements from fluid previously taken from the same device.

21. The method according to claim 17, wherein the step of classifying comprises:
   generating shape features based upon the plurality of object elements; and
   identifying a type of object wear based upon the generated shape features.

22. The method according to claim 17, wherein the step of classifying comprises:
   accessing a database to compare the imaged object elements with previously stored object element data.

23. The method according to claim 17,
   wherein after said applying step, providing each pixel of said video signal at up to 256 levels of gray corresponding to said illumination map; and
   thresholding the levels of gray of said illumination map to at least a multi-level image by designating particular pixels to predetermined levels depending upon where their intensity value is in relation to said base line illumination pattern.

* * * * *